(12) United States Patent
van Sparrentak et al.

(10) Patent No.: US 12,257,077 B2
(45) Date of Patent: Mar. 25, 2025

(54) CLAMPING DEVICES AND METHODS FOR MEASURING BLOOD PRESSURE

(71) Applicant: Tournicare Pty Ltd, Camberwell (AU)

(72) Inventors: Niels van Sparrentak, Camberwell (AU); Rohan White, Camberwell (AU)

(73) Assignee: Tournicare Pty Ltd, Camberwell (AU)

( * ) Notice: Subject to any disclaimer, the term of this patent is extended or adjusted under 35 U.S.C. 154(b) by 594 days.

(21) Appl. No.: 17/442,305

(22) PCT Filed: Mar. 23, 2020

(86) PCT No.: PCT/AU2020/050276
§ 371 (c)(1),
(2) Date: Sep. 23, 2021

(87) PCT Pub. No.: WO2020/191436
PCT Pub. Date: Oct. 1, 2020

(65) Prior Publication Data
US 2022/0151561 A1    May 19, 2022

(30) Foreign Application Priority Data
Mar. 25, 2019    (AU) ................................ 2019901000

(51) Int. Cl.
*A61B 5/00* (2006.01)
*A61B 5/022* (2006.01)
(Continued)

(52) U.S. Cl.
CPC ........ *A61B 5/6838* (2013.01); *A61B 5/02233* (2013.01); *A61B 5/6843* (2013.01); *A61B 8/04* (2013.01); *A61B 8/4209* (2013.01)

(58) Field of Classification Search
CPC .............. A61B 5/6838; A61B 5/02233; A61B 5/68431; A61B 8/04
See application file for complete search history.

(56) References Cited

U.S. PATENT DOCUMENTS 4,466,437 A * 8/1984 Dyck ........................ F16B 2/10
                                                                81/338
D287,054 S * 12/1986 Heaton ........................ D24/143
(Continued)

FOREIGN PATENT DOCUMENTS

DE     112018006685 T5 *  9/2020  ......... A61B 5/02233
EP         1369080 A1 * 12/2003  ......... A61B 5/02233
(Continued)

OTHER PUBLICATIONS

Extended European Search Report for European Application No. 20777024.9 mailed on Nov. 25, 2022, 10 pages.

*Primary Examiner* — Oommen Jacob
(74) *Attorney, Agent, or Firm* — Bret E. Field; Bozicevic, Field & Francis LLP

(57) ABSTRACT

A clamping device for reducing blood flow in a human limb comprises a first rigid part having a first inner profile, and a second rigid part having a second inner profile generally facing the first inner profile. A coupling portion couples the first rigid part and second rigid part to each other. The first inner profile extends further away from the coupling portion than the second inner profile. The first and second inner profiles define a recess, the recess being shaped to enable the clamping device to be positioned on the human limb, and the clamping device being configured to shift between an expanded configuration and a clamped configuration. The first and second inner profiles are arranged to apply pressure against the human limb when the device is in the clamped configuration and thereby to apply pressure to blood vessels in the human limb and reduce blood flow through the blood vessels.

29 Claims, 10 Drawing Sheets

(51) Int. Cl.
*A61B 8/00* (2006.01)
*A61B 8/04* (2006.01)

(56) References Cited

U.S. PATENT DOCUMENTS

| | | | |
|---|---|---|---|
| 10,307,332 B2* | 6/2019 | Cheng | A61H 39/04 |
| 2003/0055453 A1* | 3/2003 | Akerfeldt | A61B 17/132 |
| | | | 606/203 |
| 2003/0092999 A1 | 5/2003 | Goto et al. | |
| 2004/0010198 A1* | 1/2004 | Yamakoshi | A61B 5/681 |
| | | | 600/499 |
| 2006/0079792 A1* | 4/2006 | Finburgh | A61B 5/681 |
| | | | 600/503 |
| 2008/0091113 A1* | 4/2008 | Kondo | A61B 5/02225 |
| | | | 600/485 |
| 2008/0250340 A1* | 10/2008 | Dlugos | A61F 5/0056 |
| | | | 606/157 |
| 2011/0288382 A1* | 11/2011 | Finburgh | A61B 5/022 |
| | | | 600/300 |
| 2013/0158418 A1 | 6/2013 | Mizukami | |
| 2013/0165787 A1 | 6/2013 | Ukawa et al. | |
| 2016/0066925 A1* | 3/2016 | van Sparrentak | A61B 17/132 |
| | | | 606/203 |
| 2016/0175192 A1 | 6/2016 | Cheng | |
| 2017/0347893 A1* | 12/2017 | Osoegawa | A61B 5/02233 |
| 2019/0053723 A1* | 2/2019 | van Sparrentak | A61B 5/6828 |
| 2022/0151561 A1* | 5/2022 | van Sparrentak | A61B 5/6838 |

FOREIGN PATENT DOCUMENTS

| | | | | |
|---|---|---|---|---|
| JP | 2017148356 A | * | 8/2017 | A61B 17/132 |
| WO | WO2014179830 A1 | | 11/2014 | |
| WO | WO-2016101888 A1 | * | 6/2016 | A61B 5/022 |
| WO | WO-2016101890 A1 | * | 6/2016 | A61B 5/02 |
| WO | WO2017054043 A1 | | 4/2017 | |
| WO | WO2017145922 A1 | | 8/2017 | |

* cited by examiner

CLAMPING DEVICES AND METHODS FOR MEASURING BLOOD PRESSURE

TECHNICAL FIELD

The present disclosure generally relates to clamping devices and methods for blood pressure measurements. More specifically, the present disclosure relates to clamping devices configured for and methods of measuring blood pressure.

BACKGROUND

It is often important to know a person's blood pressure when assessing or monitoring their health or wellbeing. This can be performed using a conventional inflatable cuff that is secured around a limb and blood pressure can be measured using a sphygmomanometer that makes use of the oscillometric method or the auscultatory method.

International patent publication WO 2014/179730 discloses a clamping device that can be used in place of a traditional tourniquet. International patent publication WO 2017/054043 discloses a clamping device that can be used in place of a traditional inflatable cuff to perform blood pressure measurements. The contents of WO 2014/179730 and WO 2017/054043 are incorporated herein in their entireties.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

Some embodiments relate to a clamping device for reducing blood flow in a human limb comprising:
a first rigid part having a first inner profile;
a second rigid part having a second inner profile generally facing the first inner profile; and
a coupling portion that couples the first rigid part and second rigid part to each other,
wherein the first inner profile extends further away from the coupling portion than the second inner profile,
wherein the first and second inner profiles define a recess, and the recess is shaped to enable the clamping device to be positioned on the human limb,
wherein the clamping device is configured to shift between an expanded configuration and a clamped configuration, and wherein the first and second inner profiles are arranged to apply pressure against the human limb when the device is in the clamped configuration and thereby apply pressure to blood vessels in the human limb and reduce blood flow through the blood vessels.

In some embodiments, a first distal end portion of the first rigid part is angled inwardly toward the coupling portion by a greater degree than a second distal end portion of the second rigid part.

In some embodiments, a degree of concavity of the first inner profile is greater than a degree of concavity of the second inner profile part In some embodiments, the first inner profile includes a plurality of profile portions, wherein the first inner profile is curved and each of the profile portions is concave and has a different curvature.

In some embodiments, the first inner profile has a central portion with a central curvature that is less than an outer curvature at an outer portion of the curved surface. The central curvature may be greater than an inner curvature at an inner portion of the curved surface.

In some embodiments, a distal tip of the first inner profile extends further away than the second inner profile by an extension in the range of about 8 mm to 20 mm.

In some embodiments, the central curvature is defined by a central radius in the range of about 56 mm to about 76 mm.

In some embodiments, the outer curvature is defined by an outer radius in the range of about 77 mm to about 105 mm. In some embodiments, the inner curvature is defined by an inner radius in the range of about 40 mm to about 55 mm.

In some embodiments, the different curvatures of the portions are defined by a plurality of axes located within the recess, and the axes are offset from each other.

In some embodiments, the coupling portion comprises a first base portion attached to the first rigid part and a second base portion attached to the second rigid part, and the first base portion is configured to receive at least a part of the second base portion.

Some embodiments relate to a clamping device for repeated blood pressure measurements in a human limb comprising:
a rigid body configured to shift between an expanded configuration and a clamped configuration, wherein the rigid body defines a recess, comprises an inner profile within the recess, and the recess is shaped to enable the clamping device to be positioned on the human limb, and the inner profile is configured to contact the human limb when the clamping device is in a clamped configuration to thereby clamp the human limb;
pressure sensing componentry located within the rigid body and configured to repeatedly:
sense pressure oscillations from an artery in the human limb; and
output data relating to the sensed pressure oscillations; and
at least one processor configured to control the transmitting component, receive the output data from the pressure sensing componentry, and to repeatedly determine a change in blood pressure based on the received output data.

In some embodiments, the pressure sensing componentry comprises any one or more of: a pressure sensing component, an ultrasonic transmitter, and an ultrasonic sensing component. The pressure sensing componentry may comprise a piezo-electric pressure transducer.

The pressure sensing component and/or ultrasonic transmitter may be configured to transmit ultrasonic waves towards an artery in the human limb when in the clamping device is positioned on the limb, and the pressure oscillation comprises reflected ultrasonic waves.

In some embodiments, at least part of the pressure sensing componentry and/or ultrasonic transmitter is located to transmit ultrasonic waves oriented at an angle relative to the length of the artery in the range of 85° to 95°.

The clamping device may further comprise:
an expandable element arranged at least partly along the inner profile, wherein the expandable element is inflatable to apply pressure to the limb, and deflatable to reduce the pressure, when the clamping device is positioned on the limb; and
inflation components for controlling the inflation of the expandable element in a predetermined manner for blood pressure measurements.

The pressure sensing componentry may be located adjacent the expandable element.

The inflation components may comprise:
- a pump in fluid connection with the expandable element for inflating and deflating the expandable element; and
- a controller connected to the pump for controlling the pump to inflate and deflate the expandable element in a predetermined manner for obtaining blood pressure measurements over a period of time.

In some embodiments, the at least one processor is configured to determine a baseline pressure using the at least one pressure sensing componentry. The at least one processor may be configured to determine a change from the baseline pressure based on the output from the pressure sensing componentry. The at least one processor may be configured to calculate a modified blood pressure measurement based on the baseline pressure and the output from the pressure sensing componentry.

The processor may be configured to determine the phase, echo time and/or frequency of the pressure oscillation from the output of the pressure sensing componentry. The processor may be configured to determine a change in phase and/or frequency of the pressure oscillation from the output of the pressure sensing componentry.

The blood pressure measurements may be repeated at a rate greater than any one or more of: once every 5 minutes, once every 2 minutes, once every minute, once every 30 seconds, once every 15 seconds, and once every second. The blood pressure measurements may be repeated every heartbeat.

In some embodiments, the pressure sensing componentry is configured to sense pressure oscillations at a rate in the range of about 5 Hz to about 100 Hz.

In some embodiments, the processor is configured to trigger an alarm signal if the determined change is greater than a predetermined threshold.

One of the at least one processors may be a controller configured to, any one or more of:
- operate the pump to inflate the expandable element to a first pressure set-point;
- operate the pump to inflate the expandable element to a second pressure set-point that is higher than the first set-point;
- operate a pressure relief valve to deflate the expandable element; and
- stop operation of the pressure relief valve.

The controller may be configured to operate the pump to inflate the expandable element to a third pressure set point lower than the first set-point and the second-set point. The controller may be configured to operate the pump to inflate the expandable element to a third pressure set point in the range of 20 mmHg to 60 mmHg. In some embodiments, the third pressure set point is in the range of about 25 mmHg to about 55 mmHg. The third pressure set point may also be in the range of about 35 mmHg to about 45 mmHg.

The controller may be configured to operate the transmitting component to transmit an ultrasonic wave when the expandable element is inflated to the third pressure set point.

In some embodiments, the rigid body comprises:
- a first rigid part having the first inner profile;
- a second rigid part having a second inner profile generally facing the first inner profile, wherein the first and second inner profiles are arranged to contact the human limb when the device is in a clamped configuration and thereby clamp the human limb; and
- a coupling portion that couples the first and second rigid parts together.

The at least one of the first rigid part and the second rigid part may define a straight portion angled with respect to the at least one rigid part. The second inner profile may be partly straight and partly curved.

In some embodiments, the clamping device as disclosed herein further comprises a cushioning element disposed on at least one of the first inner profile and the second inner profile. The cushioning element may extend over the first inner profile and the second inner profile, may be affixed to the first inner profile and not affixed to the second inner profile.

The rigid body may partially encircle a cross-section of the human limb when placed on the limb in the clamped configuration.

The clamping device may further comprise at least one releasable retention mechanism to retain the clamping device in the clamped configuration; wherein the at least one retention mechanism is configured to allow the rigid body to adopt one of a plurality of retention positions in which the coupling portion is restrained from adopting the unclamped (or expanded) configuration.

Some embodiments relate to a clamping device for repeated blood pressure measurements in a human limb comprising:
- a rigid body configured to shift between an expanded configuration and a clamped configuration, wherein the rigid body defines a recess, comprises an inner profile within the recess, and the recess is shaped to enable the clamping device to be positioned on the human limb, and the inner profile is configured to contact the human limb when the clamping device is in a clamped configuration to thereby clamp the human limb;
- an expandable element arranged at least partly along the inner profile, wherein the expandable element is inflatable to apply pressure to the limb, and deflatable to reduce the pressure, when the clamping device is positioned on the limb;
- inflation components for controlling the inflation of the expandable element in a predetermined manner for blood pressure measurements;
- pressure sensing componentry configured to repeatedly:
  - sense pressure and pressure oscillations in the expandable element; and
  - output data relating to the sensed pressure and the reflected ultrasonic wave; and
- at least one processor configured to control the inflation components to conduct a baseline blood pressure measurement, receive the output data from the pressure sensing componentry, and to repeatedly determine a change in blood pressure based on the received output data.

Some embodiments relate to a method of repeated blood pressure measurements comprising:
- positioning a clamping device according to any one of the preceding claims on a human limb;
- clamping the human limb with the clamping device such that an inner profile of the clamping device contacts the human limb;
- outputting data from the pressure sensing componentry as a result of the pressure sensing componentry sensing pressure oscillations from an artery in the human limb;
- determining a change in blood pressure with a processor based on output data received from the pressure sensing componentry; and
- repeating the steps of sensing pressure oscillations, outputting data relating to the pressure oscillations, and determining the change to thereby repeatedly conduct blood pressure measurements.

The method may further comprise calculating a modified blood pressure measurement with a processor based on a baseline pressure and the change determined.

Calculating the modified blood pressure measurement may further comprise using a calibration curve to determine the change in blood pressure.

The method may further comprise:

inflating and deflating an expandable element of the clamping device located between the inner profile and the human limb, wherein the expandable element contacts the human limb; and calculating the baseline blood pressure measurement based on pressure readings from a pressure sensing componentry of the clamping device during the deflation of the expandable element.

The method may further comprise inflating an expandable element of the clamping device located between the inner profile to a pressure set-point to thereby apply a predetermined pressure to the human limb before sensing the pressure oscillations. The pressure set-point may be in the range of any one or more of: about 20 mmHg to about 60 mmHg, about 25 mmHg to about 55 mmHg, and about 35 mmHg to about 45 mmHg.

The method may further comprise transmitting ultrasonic waves with pressure sensing componentry of the clamping device towards an artery in the human limb such that the pressure oscillations comprise reflected ultrasonic waves.

The method may further comprise either one or both of:

determining phase and/or frequency of the reflected ultrasonic wave from the output of the pressure sensing componentry with the processor;

determining a change in phase and/or frequency of the reflected ultrasonic wave from the output of the ultrasonic sensing component with the processor of the clamping device.

The repeating blood pressure measurements may be performed at a rate greater than any one or more of: once every 5 minutes, once every 2 minutes, once every minute, once every 30 seconds, once every 15 seconds, and once every second. The repeating blood pressure measurements may be performed at a rate in the range of about of 5 Hz to about 100 Hz.

The method may further comprise triggering an alarm signal if the determined change is greater than a predetermined threshold.

Some embodiments relate to a method of repeated blood pressure measurements comprising:

positioning a clamping device as described herein on a human limb;

clamping the human limb with the clamping device such that an inner profile of the clamping device contacts the human limb;

inflating an expandable element of the clamping device located between the inner profile and the human limb to apply a pressure set-point;

outputting data from the pressure sensing componentry as a result of the pressure sensing componentry sensing pressure oscillations from an artery in the human limb;

determining a change in blood pressure with a processor based on output data received from the pressure sensing componentry; and repeating the steps of sensing pressure oscillations, outputting data relating to the pressure oscillations, and determining the change to thereby repeatedly conduct blood pressure measurements over time.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments are described in further detail below, by way of example, with reference to the accompanying drawings briefly described below. Like reference labels in the drawings indicate like features.

DETAILED DESCRIPTION

Described embodiments generally relate to devices and methods for blood pressure measurements. More specifically, embodiments relate to clamping devices configured for measuring or sensing changes in blood pressure and methods of measuring or sensing changes in blood pressure.

Conventional methods of blood pressure measurements may be time consuming and it is not possible for blood pressure to be continuously monitored (repeatedly measured over a short period of time) as the act of measurement influences the blood pressure of the person. As a result, while it is common for heart rate, heart activity (via electrocardiography) and blood oxygen saturation to be continuously monitored, blood pressure is not commonly continuously monitored.

Figure 1A:
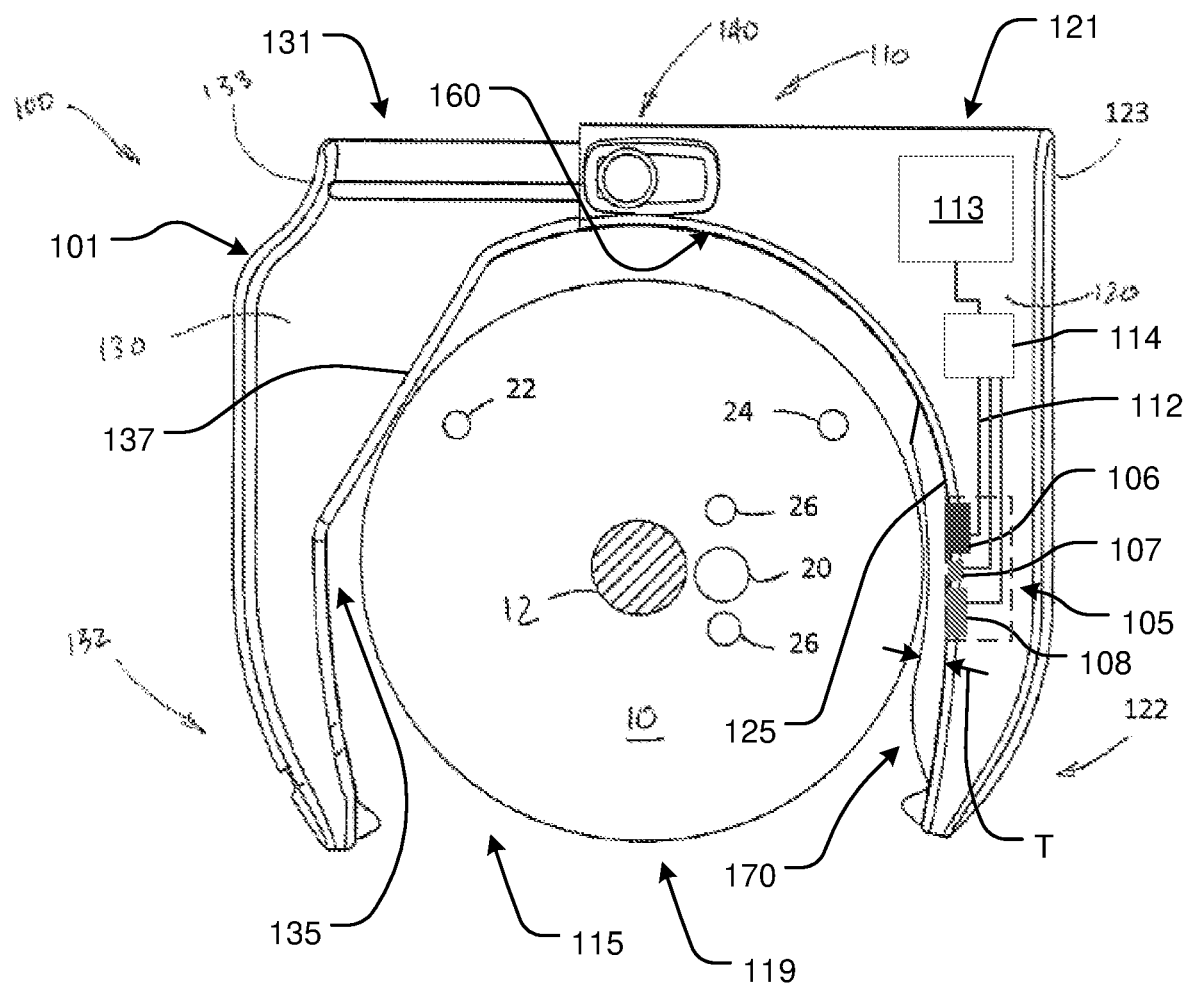
FIG. 1A is a schematic side view of a clamping device according to some embodiments positioned on a human upper arm (shown in cross-section), with the clamping device in an unclamped configuration.
Figure 1B:
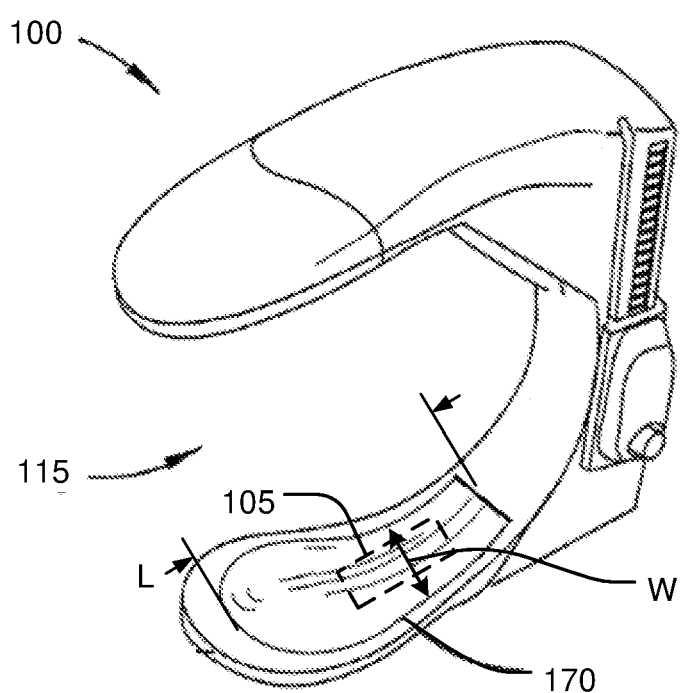
FIG. 1B is a perspective view of the clamping device of FIG. 1A.

Referring to FIG. 1, certain parts of the anatomy of an upper human arm 10 are shown for purposes of illustration of an intended use of a clamping device 100 according to some embodiments. A human limb 10 (such as an upper arm) generally has a centrally positioned humerus bone 12 around which tissues are arranged including muscles, veins and arteries. A significant artery in the upper arm 10 is the brachial artery 20 which is generally located deeper within the flesh of the upper arm 10 than the veins, such as the cephalic vein 22, basilic vein 24 and brachial veins 26. FIG. 1 shows the upper arm in an uncompressed state.

A clamping device 100 according to some embodiments is shown and described in further detail. The clamping device 100 is configured for repeatedly sensing changes in blood pressure in a human limb 10 and generally comprises a rigid body 101 that defines a recess 115. The recess 115 is shaped such that the clamping device 100 can be positioned on the human limb 10. The rigid body 101 is configured such that it is able to shift between an expanded configuration and a clamped configuration. The rigid body 101 also comprises an inner profile 125, 135 that resides within the recess 115. The inner profile 125, 135 is configured such that it contacts the human limb 10 when the clamping device 100 is in a clamped configuration to thereby clamp the human limb 10.

The rigid body 101 may comprise two main movable parts comprising the first and second rigid parts 120, 130. The first rigid part 120 (or first jaw) and the second rigid part 130 (or second jaw) are coupled by coupling portion (or bridge portion) 110. The first and second rigid parts 120, 130 may be described as arms or jaws because of their opposed relation and their function of clamping about a human limb 10. As shown in the drawings, the device 100 is generally approximately U-shaped (or C-shaped), with the coupling or bridge portion 110 joining the first and second rigid parts 120, 130 at an apex of the U-shape.

The first rigid part 120 and a second rigid part 130 are movable relative to each other so that the clamping device 100 is configurable to shift between an unclamped configuration, in which the rigid parts 120, 130 are spaced wide enough to allow the device 100 to be placed about (positioned on) or partially about a human limb 10, such as an upper arm, and a clamped configuration in which the rigid parts 120, 130 (directly or indirectly) press toward and against the lateral and medial surfaces of the limb. While embodiments are generally described as being configured for clamping a human upper arm 10, embodiments may also be configured for clamping other limb parts such as a forearm, a lower leg or an upper leg, for example.

The coupling or bridge portion 110 comprises first and second coupling parts that are each coupled, connected to or integrally formed with the rigid parts 120, 130, such that relative movement of the first and second coupling parts when the device 100 transitions between the clamped and unclamped configurations, corresponds with relative movement between the first and second rigid parts 120, 130.

The first rigid part 120 has a base portion 121 that forms part of the coupling or bridge portion 110. The second rigid part 130 also has a base portion 131 that forms part of the bridge or coupling portion 110. The first rigid part 120 also has a distal portion 122 at a free end distal of the base portion 121. The first rigid part 120 defines a generally non-linear inner profile 125 that faces an opposite non-linear inner profile 135 defined by the opposing second rigid part 130.

On an outward face of the base portion 120, there may be a land 123 and on an outward face of the base portion 131 of the second rigid part 130, there may be another land 133. The lands 123, 133 are generally arranged to be manually compressible by a human hand, such that a thumb can be placed on one of the lands 123, 133, while one or more fingers are placed on the opposite land 123, 133 so that manual force can be used to squeeze and move the rigid parts 120, 130 toward each other and thereby move the device 100 into a clamped configuration. In some embodiments, the lands 123, 133 may be arranged at opposite ends of the coupling portion 110. In other embodiments, the lands 123, 133 may be defined by oppositely directed faces of projections extending from respective parts 120, 130.

Device 100 and other device embodiments described herein advantageously allow application of the device to the left or right arm of a human. Where the inner profiles 125, 135 of the clamping two rigid parts 120, 130 are not symmetrical about the coupling portion 110, the device 100 can be readily reversed in orientation to accommodate placement on either the left or right arm.

In order to maintain the device 100 in the clamped configuration, the device 100 may have at least one retention mechanism 140. As shown in the Figures, a retention mechanism 140 may be disposed on opposite sides of the coupling or bridge portion 110. The one or more retention mechanisms 140 are configured to retain the device 100 in a compressed, clamped configuration once the rigid parts 120, 130 are moved toward each other. In particular, at least one retention mechanism 140 is configured to allow the device 100 to adopt one of a plurality of retention positions in which the coupling portion 110 is restrained from adopting an unclamped configuration.

Each retention mechanism 140 may be configured to adopt one of a plurality of discrete retention positions as the rigid parts 120, 130 are moved from an unclamped configuration to a clamped configuration. The specific discrete retention position adopted in the clamped configuration will depend on the size of the limb about which the device 100 is positioned as well as the degree of compressive force applied in manually driving the rigid parts 120, 130 toward each other. Each retention mechanism 140 may comprise a ratcheting retention mechanism (not shown).

The shape of the device 100 can be described as generally C-shaped or U-shaped, depending on the device orientation, featuring an opening 119 between the opposed first and second distal portions 122, 132, with the bridge 110 at the apex opposite the opening 119. The space interior of the first and second rigid parts 120, 130 is thus generally concave to accommodate a limb and can be flattened as the rigid parts are pressed inwardly to close about the limb. At a minimum, at least one of the first inner profile 125 and the second inner profile 135 is generally non-linear. This non-linearity may take the form of a somewhat concave curvature along the respective rigid part inner profile or a partially straight and partially curved profile. The first and/or second non-linear inner profile 125/135 may have two or more straight sections (angled relative to each other or separated by a curved section) and/or may have two or more sections of different curvature.

In the device 100 shown in FIG. 1, the first inner profile 125 is curved in a somewhat concave manner to be pressed against the medial surface of the limb 10 and the second inner profile 135 has a first slightly curved section 136 near the bridge apex (corresponding to the coupling portion 110), a generally straight section 137 that is angled relative to the curved section 136 and angled relative to a longitudinal axis of the bridge (along which relative movement occurs) and a second slightly curved section 138 that is angled relative to the straight section 137 and extends to the distal end 132. The second curved section 138 may be generally straight in some embodiments. The straight section 137 need not be perfectly straight. The purpose of the straight section 137 is to apply direct pressure to the cephalic vein 22 when the device 100 is placed over an upper arm 10. The configuration of the second inner profile 135, including straight section 137, is therefore arranged to apply pressure generally inwardly to the lateral side of the upper arm 10 but in particular to the top or upper lateral part of the upper arm 10.

The clamping device 100 further comprises pressure sensing componentry 105. The pressure sensing componentry 105 may, for example form part of a pressure sensor. The pressure sensing componentry 105 is located in clamping device 100 to either directly or indirectly sense pressure and/or pressure oscillations on at least a part of the inner profile 125, 135 (or inner face) of one or both of the first and second rigid parts 120, 130. For example, the pressure may be applied to a component of the clamping device 100 such as a cushioning element 160 or an expandable element 170 connected to the inner profile 125, 135. In some embodiments, the pressure sensing componentry 105 is located in the body 101 and pneumatically connected to the expandable element 170 to sense pressure and/or pressure oscillations in the expandable element 170. The pressure sensing componentry 105 is therefore suitably arranged to sense a clamping pressure applied to a limb 10 when the clamping device 100 is in a clamped configuration on the limb.

The pressure sensing componentry 105 may comprise one or more pressure sensor components 106, which maybe pressure transducer element such as a piezoelectric element. The piezoelectric element may be operated (excited) using constant current circuitry. The pressure sensing componentry 105 may also be configured to output data relating to the sensed pressure or pressure oscillations.

The pressure transducer element 106 may be electrically coupled via suitable insulated conductors 112 to provide an output signal to a display 113. The display 113 may be, for example, a segmented LCD display. The display 113 may be used to indicate (in response to the received output signal) the pressure sensed by the pressure sensing componentry 105 and/or the pressure transducer element 106, so that a person, such as a health professional or medical practitioner, can readily view the display 113 and ascertain whether the clamping device 100 has been applied with too much compression, not enough compression or a degree of compression that is appropriate. In some embodiments, a compression pressure (cuff pressure) is applied at a set-point less than the diastolic blood pressure in the human arm 10. For example, a compression pressure of about 40 mmHg (5.333 kPa) may be applied. In some embodiments, the compression pressure may be, for example, between about 20 mmHg and about 60 mmHg.

In some embodiments, the pressure sensing componentry 105 may be connected to the display 113 via a processor 114. The display 113 may therefore be used to display the results of calculations by the processor 114 such as blood pressure measurements. The display 113 may also provide a visual indication that a change in blood pressure has been determined.

Figures 2A, 2B:
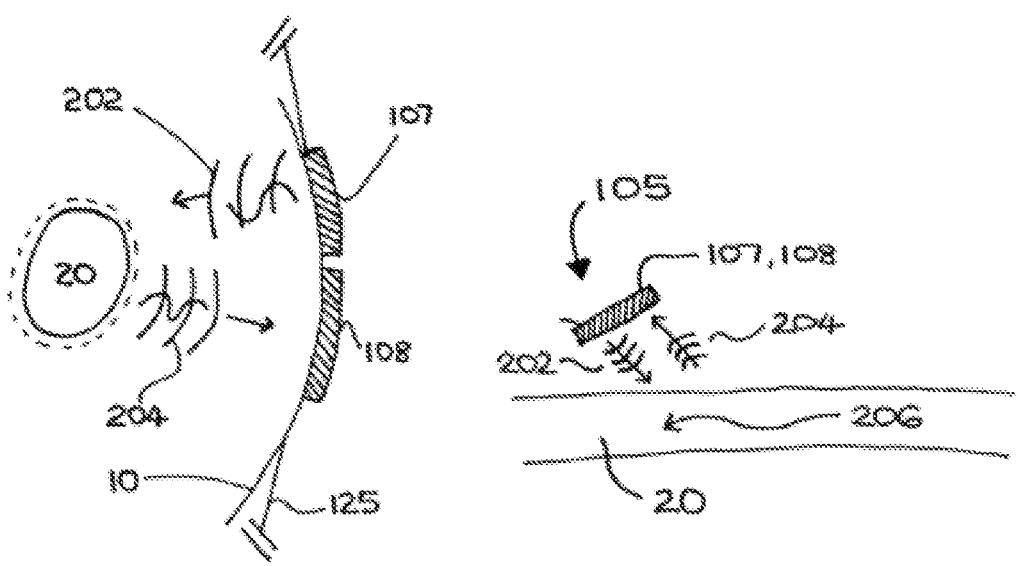
FIG. 2A is a schematic cross-sectional view of pressure sensing componentry transmitting an ultrasonic wave into the human upper arm and a pressure oscillation produced by the brachial artery in the human upper arm.
FIG. 2B is a schematic side view of pressure sensing componentry transmitting an ultrasonic wave into the human upper arm and a pressure oscillation from the brachial artery in the human upper arm.

Referring to FIGS. 2A and 2B, the pressure sensing componentry 105 may also be configured to transmit acoustic or pressure waves such as ultrasonic waves 202 towards the artery 20 in the human limb 10 when the clamping device 100 is positioned on the limb. The pressure sensing componentry 105 may be located in the clamping device 100 such that when the clamping device 100 is positioned on the human limb 10, the transmitted ultrasonic waves 202 travel along a path at an acute angle relative to the length of the artery 20 that is roughly aligned with the direction of blood flow 206 within the artery 20. The angle between the direction of the transmitted ultrasonic waves 202 (and therefore the reflected waves 204) may, for example, be less than about 85° relative to the length of the artery 20. Put another way, the angle between the direction of the ultrasonic waves 202, 204 should not be within 5° of the normal to the length of artery 20.

As a result of the transmitted ultrasonic waves 202 impinging the artery 20, a pressure oscillation 204 in the form of a reflected (echoed) ultrasonic (or acoustic) wave may be produced. The frequency or phase of the reflected ultrasonic (or acoustic) wave may be shifted from that of the transmitted ultrasonic wave 202. This may be the result of the Doppler effect dependent on the velocity of blood flowing through the artery 20. Moreover, a change in blood pressure generally has an effect on the velocity of blood flowing through the artery 20. Higher blood pressure is generally associated with higher velocity blood flow. A change in velocity of blood flow therefore causes a change in the frequency shift of the reflected ultrasonic wave 204. The change in the frequency shift may be proportional to the change in velocity of blood and/or the blood pressure in the artery 20.

In some embodiments, the pressure sensing componentry 105 is configured to transmit pulsed ultrasonic waves. The pulsed ultrasonic waves may have a pulse length in the range of about 1 microsecond to about 10 milliseconds. The pulses may be transmitted and sensed at a rate of about 5 Hz to about 100 Hz. To obtain measurements every heartbeat, pulses should be transmitted at a rate greater than the heartbeat to enable sensing of several reflected ultrasonic wave pulses. For example, a sensing rate greater than say 2 Hz may enable measurement of blood pressure every heartbeat for a heart rate of less than 120 beats per minute.

The pressure sensing componentry 105 may be configured to receive and sense a pressure oscillation 204, such as the reflected ultrasonic wave. In some embodiments, the pressure oscillation 204 is produced by a pulsating artery 20 (such as the brachial artery) in the human limb 10. The pressure sensing componentry 105 may also be configured to output data (or an electrical signal) relating (or corresponding) to the sensed pressure oscillation 204. Changes in blood pressure may lead to further changes to any one or more of: the intensity of the pressure oscillation 204, a shift in frequency or phase of the reflected ultrasonic wave 204, or a delay (echo) time between a transmitted and sensed pressure oscillation 204. A change in the output may therefore be indicative of a change in blood pressure as measured from the artery 20. For example, an increased frequency or larger frequency shift may indicate an increased blood pressure and a reduced frequency or smaller frequency shift may indicate a reduced blood pressure. An increase in blood pressure may lead to dilated blood vessels and thereby reduced the echo time as the blood vessel walls may be closer to the pressure sensing componentry 105. Conversely, a decrease in blood pressure may lead to contracted or less-dilated blood vessels and thereby increase the echo time.

In some embodiments, the pressure sensing componentry 105 further comprises one or more ultrasonic transmitters 107 and one or more ultrasonic sensing components 108. The ultrasonic sensing components 108 may be configured and located to receive and sense the pressure oscillations 204 such as reflected (echoed) ultrasonic waves.

The pressure sensing componentry 105 may comprise a piezoelectric element configured to perform all of the functions of the pressure transducer element 106, the ultrasonic transmitter 107 and the ultrasonic sensing component 108.

In some embodiments, the clamping device 100 comprises amplification circuitry or amplification components to amplify the output from the pressure sensing componentry 105. The output from the pressure sensing componentry 105 may be transmitted or supplied to a processor 114. The clamping device 100 may also comprise one or more analogue to digital converters for digitising the output before being transmitted to the processor 114.

Although the pressure sensing componentry 105 is shown in FIG. 1 as being disposed in the first rigid part 120 the pressure transducer element may be positioned at a different position around the inner profile of the clamping device 100. For example, the pressure transducer element (such as a pressure sensor) being positioned adjacent the inner profile 125 extending along the inside of the first rigid part 120. Additionally, more than one pressure transducer element 106 may be positioned around the inner profile of the clamping device 100, either coupled via additional conductors 112 to the same display 113 and/or processor 114. The additional pressure transducer element 106 may be part of the pressure sensing componentry 105.

Device 100 may have a cushioning element 160 that extends around (or mostly around) an inner periphery of the bridge 110 and first and second rigid parts 120, 130. This cushioning element 160 therefore covers at least part of one or more of the first inner profile 125 and the second inner profile 135. The cushioning element 160 may be freely slidable with respect to the second rigid part 130 along the second inner profile 135 to allow for accommodating the relative movement between the first and second arms 120, 130 during clamping and unclamping.

The clamping device 100 may also comprise an expandable element 170. The expandable element 170 may comprise an inflatable bladder for applying pressure to at least part of an arm 10, for example when used to clamp the arm or when used to take blood pressure measurements.

The expandable element 170 may form part of a core of the cushioning element 160 and may extend at least partially along the longitudinal axis of the cushioning element 160, optionally all the way to the end of the cushioning element 160, but possibly extending only in the order of a ½ to ⅘ of the length of the cushioning element 160. The pressure applied by the expandable element 170 may be measured by the pressure sensing componentry 105.

The expandable element 170 may be formed as a separate part from the cushioning element 160, even though the expandable element 170 may be co-located and at least partially co-extensive therewith. In some embodiments, device 100 is provided with an expandable element 170 within, under or co-located with a cushioning element 160.

The expandable element 170 has a width W, running along the length of the human limb 10 when positioned on the human limb 10, in the range of about 40 to about 60 mm. The width W of the expandable element 170 is transverse to the length of the first rigid portion 120 or second rigid portion 130 that the expandable element 170 is adjacent to. This assists in enabling a sufficient portion of blood vessels in the human limb 10 to be compressed and provide sufficient occlusion of the blood vessels (in particular the arteries) by the clamping device 100, 2600 when the expandable element 170 is inflated. If the width W of the expandable element 170 is smaller than the range above, this may result in insufficient occlusion of blood vessels. If the width W is larger than the range above, this may lead to the maximum amplitude of the pressure oscillations in the blood vessels incorrectly occurring at a lower pressure which may lead to inaccurate blood pressure measurements.

The expandable element 170 may have a length L along the inner portion 125 in the range of about 5 cm to about 36 cm. The length L may, in some embodiments, be in the range of about 5 cm to about 18 cm. The length L may, in some embodiments, be in the range of about 18 cm to about 36 cm. The length L may, in some embodiments, be in the range of about 5 cm to about 10 cm. The length L of the inner portion 125 at the upper end of the range may therefore enable the expandable element 170 to contact up to half or over half the circumference of the human limb 10.

When the lamping device 100 is placed on the human limb 10, the expandable element 170 may have a thickness T, when inflated against the human limb 10, in the range of about 5 mm to about 5 cm. The thickness T may, in some embodiments, be in the range of about 1 cm to about 3 cm.

In some embodiments, the pressure sensing componentry 105 is located within the rigid body 101 and adjacent the expandable element 170. For example, the pressure sensing componentry 105 may be located in the first rigid part 120. This enables the pressure sensing componentry 105 to be located near portions of the inner profile 125, 135 that are in intimate contact with that human limb 10 to assist in the transmission and sensing of pressure oscillations 202, 204, such as ultrasonic waves.

Figure 3:
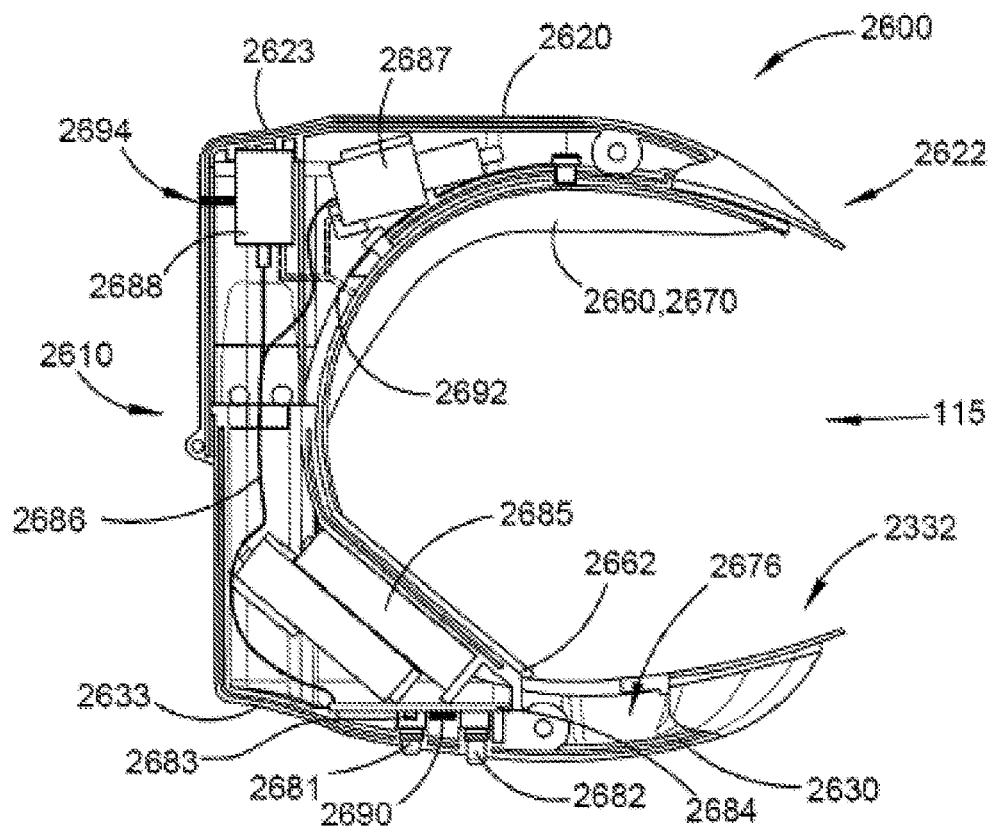
FIG. 3 is a cross-sectional view of a clamping device.
Figure 4:
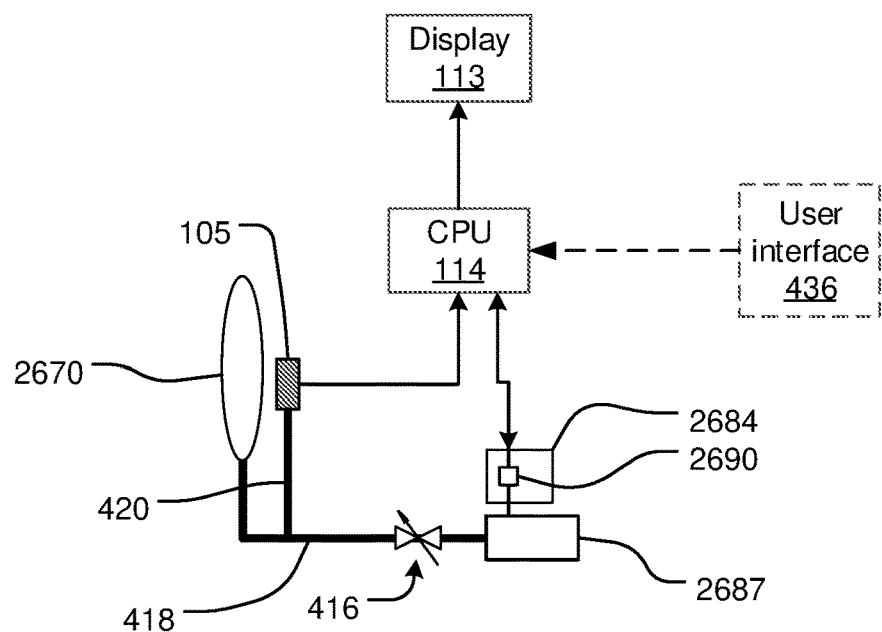
FIG. 4 is a block diagram of components of the clamping device of FIG. 1A according to some embodiments.
Figure 5:
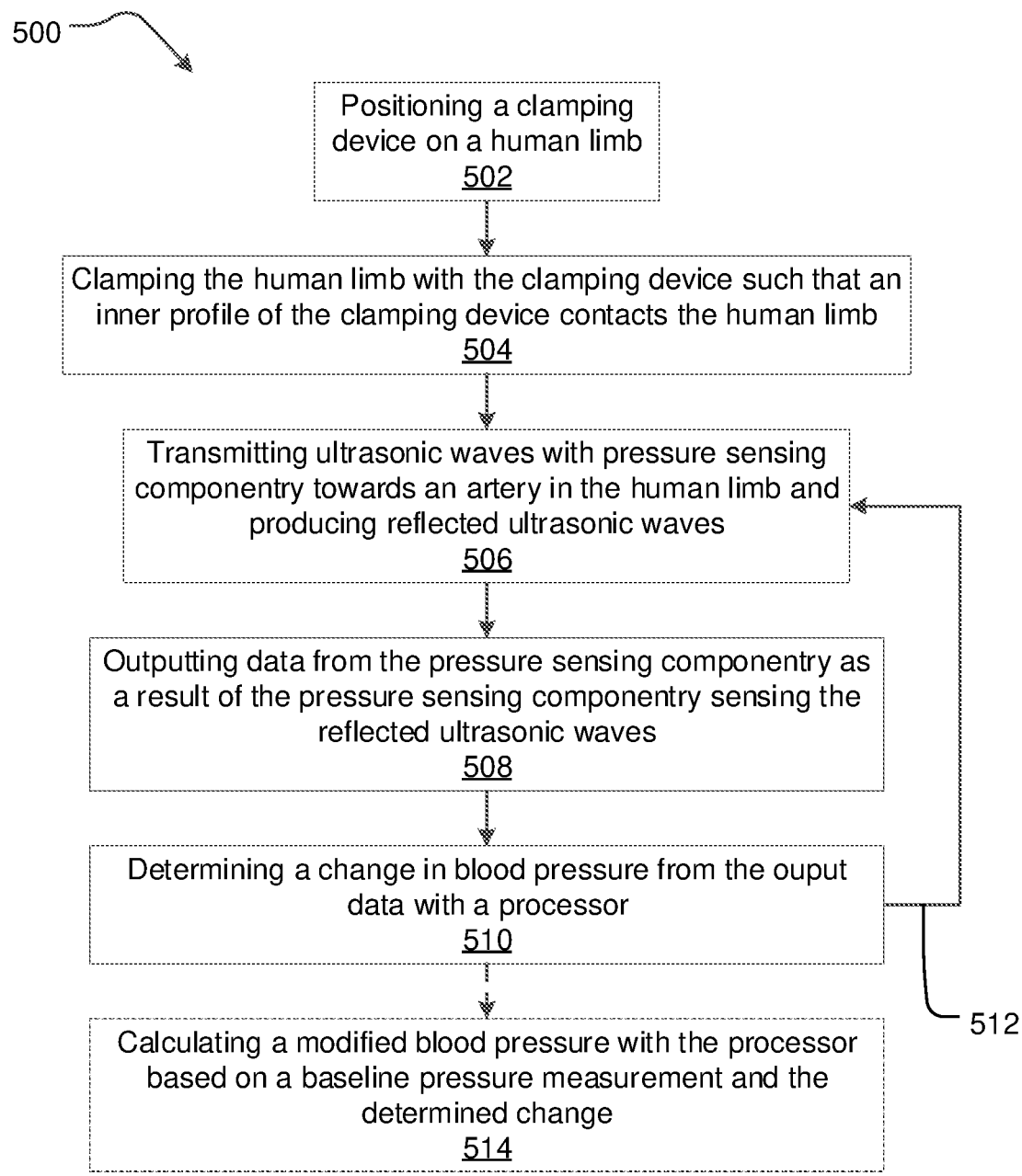
FIG. 5 is a flow chart illustrating a method of repeatedly sensing changes in blood pressure according to some embodiments.
Figure 6:
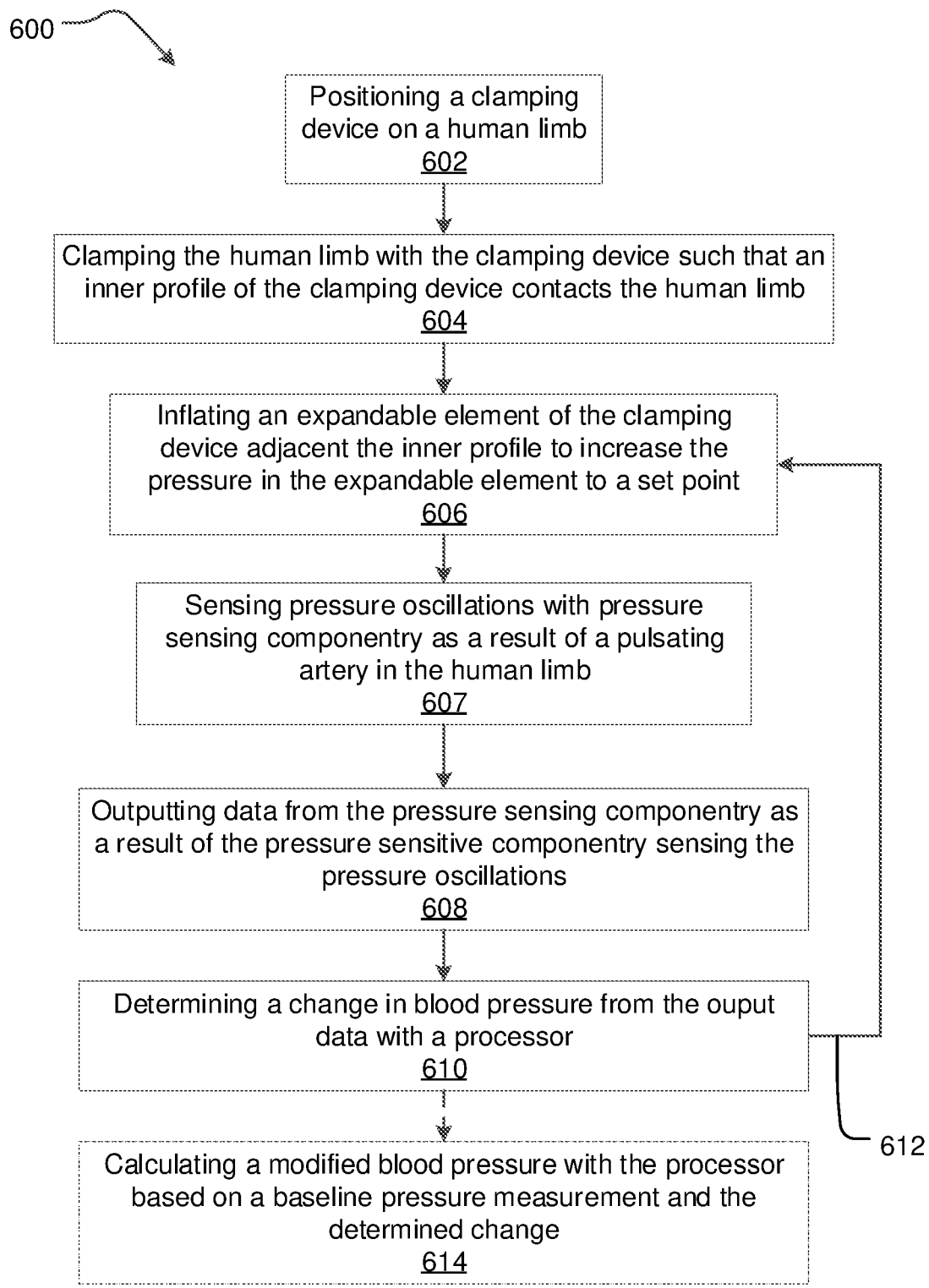
FIG. 6 is a flow chart illustrating a method of repeatedly sensing changes in blood pressure according to some embodiments.

Referring to FIGS. 3 and 4, the clamping device 100, 2600 may further comprise electronic components such as at least one processor 114 and/or controller 2690 configured to control the clamping device 100 and obtaining blood pressure measurements in an autonomous manner once the clamping device 100 has been correctly positioned and clamped onto the arm and measurement has been initiated (for example by depressing a button or switch).

The clamping device 100, 2600, further comprises a pump 2687 and controller 2690. The expandable element 170, 2670 may be coupled to the pump 2687 via a suitable coupling valve (416). The expandable element 170, 2670 may be coupled to the pump 2687 via a fluid conduit 418 to pump air into and release air from the expandable element 170, 2687 via the coupling valve 416. The pump 2687 may, for example, be a rotary pump.

In some embodiments, the controller 2690 provides control functions that enable automated inflation and deflation of the expandable element 170, 370, 2670, such control functions may be provided by a controller 2690 on a circuit board 2684 that is electrically coupled to a pump 2687 to operate the pump 2687 to pump air into (inflate) the expandable element 2670.

The controller 2690 may comprise processor 114 and processor 114 may be configured to provide the described functions of controller 2690. The controller 2690 may, however, comprise another processor (not shown) in addition to processor 114. In some embodiments, the processor 114 is part of the circuit board 2684. The circuit board 2684 may form part of a blood pressure monitoring module. In some embodiments, the pressure sensing componentry 105 may also be part of the circuit board 2684.

The controller 2690 is also electrically coupled to a pressure relief valve 2688 (for example in the form of a small solenoid valve) to control operation of the pressure relief valve 2688 and thereby selectively allow deflation of the expandable element 2670. The controller 2690 may control operation of the pressure relief valve 2688 to selectively allow progressive and/or staged deflation of the expandable element 2670, for example in a set or programmed manner that allows blood pressure measurements to be taken using the pressure sensor 2110. The pump 2687 may be positioned inside either the first part 2620 or the second part 2630, although in the illustrated embodiment, the pump is disposed in the first part 2620. A suitable air inlet 2694 may be provided in an external wall of the part of the device 2600 within which the pump 2687 is housed. The air inlet 2694 may also function as an air outlet during deflation or there may be a separate air outlet provided in an external wall of the device 2600.

In some embodiments, the pressure relief valve 2688 may be a fail-safe valve that is only closed when powered and opens to vent or inflate the expandable element 170, 2670 in the event of a lack of power or loss of power.

Manually actuable input components may be positioned on an outside of one of the first part 2620 and the second part 2630 and can be used to provide user control input to the controller 2690, for example via inflation and deflation actuators 2681 and 2682. The inflation actuator 2681, which may be formed as a button, and a deflation actuator 2682, which may be formed as a deflation button, may be coupled to the circuit board 2684. The actuators 2681, 2682 may be arranged to interact with the controller 2690 to cause the controller 2690 to send control signals via separate electrical conductors (e.g. wires) 2686 to the pump 2687 and the pressure relief valve 2688, respectively, to cause inflation or deflation of the expandable element 2670.

The inflation and deflation actuators 2681, 2682 may be positioned close to each other on an external (outwardly facing) wall of the second part 2630, in between a land 2633 (for applying manual force to bring the device 2600 toward a clamped configuration) and a distal end 2632 of the second part 2630, as is shown in the Figures. Alternatively, the inflation and deflation actuators 2681, 2682 may be positioned close to each other on an external (outwardly facing) wall of the first part 2620, in between a land 2623 (for applying manual force to bring the device 2600 toward a clamped configuration) and a distal end 2622 of the first part 2630. In either case, it is preferred that the inflation and deflation actuators 2681, 2682 are positioned on a part of the device 2600 that is away from the bridge portion 2610. In a further alternative, the inflation and deflation actuators 2681, 2682 may be positioned on a part of the bridge portion 2610 that does not interfere with relative movement between the first and second parts 2620, 2630 and does not interfere with the clamping or unclamping functions of the device 2600.

Inflation of the expandable element 170, 2670 by the pump 2687 may be controlled by the controller 2690 to achieve an internal pressure of the expandable element 2670 at a first pressure set-point or at a second pressure set-point that is higher than the first set-point. The first pressure set-point may be a pressure from about 40 mmHg to about 80 mmHg, and optionally about 60-70 mmHg (e.g. greater than an expected diastolic pressure). The second pressure set-point may be a pressure from about 80 mmHg to about 400 mmHg, and optionally about 90-100 mmHg (e.g. greater than an expected systolic pressure).

The pressure relief valve 2688 may be in communication with an air inlet/outlet 2694 in an external wall of the first part 2620 (for embodiments where the pressure relief valve 2688 and the pump 2687 are in the first part 2620). The pump 2687 may in some embodiments be in fluid (and/or pneumatic) communication with a separate air inlet/outlet (not shown) to inlet/outlet 2694. Small tubing 2692 may be provided inside the device housing to pneumatically couple the pump 2687, the expandable element 2670 and the relief valve 2688 so that air can be pumped into the expandable element 2670 and released therefrom via the relief valve 2688.

Referring to FIG. 4, the pressure sensing componentry 105 may be coupled to the expandable element 170, 2670 via a fluid conduit 420. The fluid conduit 420 may be in fluid or pneumatic communication with fluid conduit 418 or may in direct fluid or pneumatic communication with the expandable element 170, 2670. In some embodiments, the pressure sensing componentry 105 is coupled to the expandable element 170, 2670 via fluid conduit 418. For example, the pressure sensing componentry 105 may be at least partially located in fluid conduit 418.

The pressure sensing componentry 105 may be used to sense the pressure in the expandable element 170, 2670 and to provide an output signal indicative of the sensed pressure in the expandable element 170, 2670 to the controller 2690 or the processor 114. As discussed below, the processor 114 may use the output signal from pump 2687 to calculate the blood pressure values in the arm 10. Alternatively, the pump 2687 may have a pressure sensing function and may provide an output signal to the controller 2690 indicative of the sensed pressure in the expandable element 170, 2670. With the output signal providing feedback, the controller 2690 can relatively accurately cause the expandable element 170, 2670 to reach the desired pressure set-point.

The pressure sensing componentry 105 is adapted to produce and send an output indicative of the sensed pressure, during progressive deflation of the expandable element 170, 2670 to processor 114 which may be configured to calculate of a set of blood pressure values in human upper arm 10 (i.e. the systolic and diastolic blood pressure values) using the oscillometric method. For example, the clamping device 2600 can be used to apply a clamping pressure to the arm 10, via the inflatable element 2670, that is above the systolic blood pressure of the subject being tested. The clamping pressure can then be reduced and blood pressure measurements made using the oscillometric method and pressure outputs from the pressure sensing componentry 105. The data indicative of the blood pressure values may then be displayed on display 113.

The pressure sensing componentry 105 can be used to reliably apply a predetermined clamping pressure (set-point) on the human upper arm 10. In some embodiments, if the expandable element 170, 2670 is partially inflated (e.g. to a pressure up to about 40 mmHg), the pressure sensing componentry 105 that is pneumatically coupled to the expandable element can be used to determine the clamping pressure. The pressure sensing componentry 105 is electrically coupled with a processor 114 (such as a CPU), which can be used to trigger an indicator when the clamping pressure has reached the predetermined pressure as described earlier. Clamping to the predetermined pressure may ensure that there is sufficient contact between the inner profile 125, 135 and the human limb to enable efficient and reliable sensing of pressure oscillations 204 and/or transmission and sensing of ultrasonic waves 202 as discussed above.

The clamping device 100, 2600 may comprise a user interface 436 to receive inputs from a user. For example, inputs may be receive to cause the processor 114 and/or controller 2690 to begin blood pressure measurements or to begin transmission and sensing of ultrasonic waves 202, 204 and determining a change in blood pressure.

In some embodiments, the user interface 436 may comprise audio components to provide a voice activation function that allows the inflation or deflation of the clamping device 2600 to be effected by voice commands.

The clamping device 100, 2600 may comprise a storage medium (not shown) for storing instructions that are executable on processor 114 or data from sensor outputs or calculations from the processor 114.

The clamping device 100, 2600 may comprise data outputs and interfaces to enable data to be recorded on external devices for later analysis and/or to assist a healthcare profession to monitor a patient's blood pressure. For example, the clamping device 100, 2600 may include a wireless transmitter or a serial data port such as a USB port.

Optionally, one or more indicators or coloured lights, such as light emitting diodes (LEDs) 2683, may also be provided on (or otherwise coupled to) the circuit board 2684 and may be associated with each of the actuators 2681, 2682. When one of the actuators 2681, 2682 has been manually actuated, the controller 2690 may cause one or more of the LEDs 2683 to light up to visually indicate that inflation or deflation is occurring or is about to occur or to indicate a particular status of operation of the device 2600. In some embodiments (described below) where the inflation or deflation can be effected automatically through voice commands or externally originating control commands, the LEDs 2683 may be used to indicate the operational status (e.g. mid-level inflation, maximum level inflation, deflation or progressive (staged) deflation) of the expandable element 2670. In other embodiments, indication of the operational status is provided on display 113.

In some embodiments, the clamping device 100, 2600 is battery powered. One or more batteries 2685 housed within the second part 2630 may provide power for the controller 2690, the circuit board 2684, the LEDs 2683, the pump 2687, the relief valve 2688, plus any other external communication function, such as an audible alarm or a wireless communication function. Although not shown, terminals of the one or more batteries 2685 are electrically coupled to the circuit board 2684 to provide a power source for the circuit board 2684. The other powered components, such as the LEDs 2683, relief valve 2688, pump 2687 and controller 2690, may receive power from the one or more batteries 2685 directly or via the circuit board 2684.

In some embodiments, the clamping device 2600 may include a visual and/or audio indicator. The visual indicator is capable of producing a visible output for humans and the audio indicator is capable of producing an audible output for humans. In some embodiments, the indicator includes a light emitting device (LED) and/or a speaker. The indicator is connected to the pressure sensing componentry 105 and the processor 114 and device 2600 may also include a user input 436 to allow a user to set a predetermined pressure value (set-point). The indicator may be triggered by the processor 114 to indicate when the sensed pressure reaches the predetermined pressure (set-point) or if the change in blood pressure exceeds a predetermined threshold. For example, the processor may generate an alarm signal transmitted to the indicator when the sensed pressure or change in pressure reaches (or exceeds) the predetermined pressure, threshold or set-point. Triggering the indicator may include lighting up the LED and/or producing a human audible sound. The provision of an indicator assists an operator of the clamping device 2600 in reliably applying a clamping pressure to the arm at the predetermined pressure value (set point). An insufficient clamping pressure may lead to inaccurate blood pressure measurements taken with clamping device 100, 2600.

Referring to FIGS. 7A to 7E, a clamping device 700 according to some embodiments is described. Generally, some embodiments relate to a clamping device 100, 700, 2600 comprising a first rigid part 120, 720 and a second rigid part 130, 730. The clamping device 100, 700, 2600 is configured to shift between an expanded (unclamped) configuration and a clamped configuration. The first rigid part 120, 720 has a first inner profile 125, 725 and the second rigid part 130, 730 has a second inner profile 135, 735 which generally faces the first inner profile 125, 725. The first and second inner profiles 125, 135, 725, 735 are arranged to apply pressure against the human limb 10 when the device 100, 700, 2600 is in the clamped configuration and thereby apply pressure to blood vessels 20, 22, 24 in the limb 10 and reduce blood flow through the blood vessels.

The clamping device 100, 700, 2600 may comprise a coupling portion 110, 710. The coupling portion 110, 710 may comprise a first base portion 121, 721 and a second base portion 131, 731. The first base portion 121, 721 is connected to the first rigid part 120, 720 and the second base portion 131, 731 is connected to the second rigid part 130, 730. At least part of the second base portion 131, 731 may be received by the first base portion 121, 721. Progressively more of the second base portion 131, 731 may be received by the first base portion 121, 721 as the clamping device 100, 700, 2600 shifts from an expanded (unclamped) configuration to a clamped configuration. The first rigid part 120, 720 and the second rigid part 130, 730 may move in a direction along the length of the coupling portion 110, 710 as the clamping device 100, 700, 2600 shifts between the expanded configuration and the clamped configuration.

In some alternative embodiments, at least part of the first base portion 121, 721 may be received by the second base portion 131, 731.

The first and second inner profiles 125, 135, 725, 735 define a recess 115, 715, and the recess 115, 715 is shaped to enable the clamping device 100, 700, 2600 to be positioned on the human limb 10. The first inner profile 725 is curved and comprises a plurality of portions with different curvatures. For example, the first inner profile 725 may comprise two or three portions with different curvatures.

In some embodiments, the first inner profile 125, 725 comprises a central portion 726 with a central curvature defined by a central radius of curvature RC relative to a first (central) axis 716. The first axis 716 passes through the recess 715 and is perpendicular to the length of the coupling portion 710 and the line 701 between the inner profiles 725, 735. The central portion 726 may extend over a length of the first inner profile 125, 725 in the range of about 28 mm to about 38 mm. In some embodiments, the central portion 726 may extend over a length of the first inner profile 125, 725 of about 32 mm.

The first inner profile 125, 725 may further comprise an inner portion 727 with an inner curvature defined by an inner radius of curvature RI relative to a second axis 717. The second axis 717 passes through the recess 715 and is perpendicular to the length of the coupling portion 710 and the line 701 between the inner profiles 725, 735. The inner portion 727 may extend over a length of the first inner profile 125, 725 in the range of about 20 mm to about 30 mm. In some embodiments, the inner portion 727 may extend over a length of about 25 mm.

The inner radius of curvature RI may be smaller than the central radius of curvature RC and the outer radius of curvature RO. The inner axis 717 may pass through the recess 715 and be at an off-centre location that is away from the central axis 716 and the outer axis 718 towards the coupling portion 110, 710. The inner axis 717 may be located closer to the coupling portion 110, 710 and the first inner profile 125, 725 than the central axis 716 and the outer axis 718.

The first inner profile 125, 725 may further comprise an outer portion (or distal arm portion) 728 with an outer curvature defined by an outer radius of curvature RO relative to an third (outer) axis 718. The third axis 717 passes through the recess 715 and is perpendicular to the length of the coupling portion 710 and the line 701 between the inner profiles 725, 735. The third radius of curvature RO may be greater than the first radius of curvature RC.

The outer portion 728 may extend over an length of the first inner profile 125, 725 in the range of about 90 mm to about 110 mm. In some embodiments, the central portion 726 may extend over a length of about 100 mm.

The central portion 726, inner portion 727, and outer portion 728 may collectively form a continuous surface of the first inner portion 125, 725.

The first axis 716 and the second axis 718 may pass be offset from each other. The central axis 716 may be located near the centre of the recess 715 when the clamping device is in the expanded configuration. In some embodiments, the outer axis 718 is offset from the central axis 716. The outer axis 718 may be located off-centre in the recess 715 away from the central axis 716 and the first inner profile 125, 725 towards the second inner profile 135, 735. The outer axis 718 may be located away from the central axis 716 towards the opening 719.

The curved first inner profile 125, 725 is concave and has a depth D of the curve between an apex 725a and a distal (or anterior) tip 729 of the first inner profile 125, 725. The depth D may be in the range of about 15 mm to about 50 mm. In some embodiments, the depth D is in the range of about 20 mm to about 40 mm. For example, the depth D may be about 30 mm.

In some embodiments, the central radius of curvature RC may be in the range of about 56 mm to about 76 mm. The central radius of curvature RC may be in the range of about 60 mm to about 70 mm. The central radius of curvature RC may, for example, be about 65 mm.

In some embodiments, the inner radius of curvature RI is in the range of about 40 mm to about 55 mm. The inner radius of curvature RI may be in the range of about 45 mm to about 53 mm. The inner radius of curvature RI may, for example, be about 50 mm.

In some embodiments, the outer radius of curvature RO is in the range of about 77 mm to about 105 mm. The outer radius of curvature RO may be in the range of about 85 mm to about 95 mm. The outer radius of curvature RO may, for example, be about 90 mm.

In the expanded configuration, the recess 115, 715 may have a width measured along a line 701 between the opposed inner surfaces 735 and 725 passing through the first axis 716, with line 701 being parallel to the direction of contraction/expansion of the first and second parts 720, 730 along the length of the coupling portion 110, 710 (in the direction of contraction and expansion). The width may be in the range of about 100 mm to about 130 mm. In some embodiments, the width in the expanded configuration may be in the range of about 110 mm to about 120 mm. The width may, for example, be about 116 mm.

The fully clamped configuration is a configuration in which the recess 115, 715 has been reduced to its minimum size. The difference between the width in the expanded configuration and the fully clamped configuration is dependent on the range of motion between the first rigid part 120, 720 and the second rigid part 130, 730. In a fully clamped configuration, the recess 115, 715 may have a width in the range of about 50 mm to about 90 mm. In some embodiments, the width in the fully clamped configuration may be in the range of about 60 mm to about 80 mm. The width may, for example, be about 70 mm. In the fully clamped configuration, the distance between the two distal tip portions 729, 739 will be less than the width (distance) separating the first and second rigid parts 720, 730 along line 701.

In some embodiments, the first rigid part 120, 720 and the second rigid part 130, 730 may extend away from the coupling portion 110, 710 such that the distal tip 729 of the outer portion 728 of the first inner portion 125, 725 extends further away from the coupling portion 110, 710 than a respective distal lateral tip 739 of a second outer portion 738 of the second inner portion 135, 735. The first inner portion 125, 725 therefore has a greater extension from the coupling portion 110, 710 than the second inner portion 135, 735.

The distance of extension E of the distal tip 729 away from the respective distal tip 739 perpendicular to the line 701 and the coupling portion 710 may be in the range of about 8 mm to 20 mm. In some embodiments, the extension E is in the range of about 10 mm to about 15 mm. The extension E may, for example, be about 13 mm.

The selected variation in curvature of the first inner profile 125, 725 and the greater distal extension of the first rigid part 120, 720 compared to the second rigid part 130, 730 (in other words the shape and configuration of the clamping device 100, 700, 2600) may advantageously assist in ensuring that the clamping device 100, 700, 2600 reliably and consistently clamps onto the human limb 10 when in the clamped configuration. In particular, the shape and configuration of the clamping device 100, 700, 2600 assists in ensuring that the clamping device 100, 700, 2600 reliably and consistently remains clamped onto the human limb 10 as the expandable element 170, 770, 2670 expands and contracts during a blood pressure measurement using the oscillatory method.

In some embodiments, the first transverse width W1 of the first inner portion 125, 725 may be larger than the second transverse width W2 of the second inner portion 135, 735. The transverse width W1 is larger so the internal limb-engaging area of the first rigid portion 120, 720 is large enough to accommodate and support the expandable element 170, 770, 2670 across most or all of the width W1. The first transverse width W1 may be slightly larger than the width W of the expandable element 170, 770, 2670. In some embodiments, the first transverse width W1 is in the range of about 43 mm to about 63 mm.

In some embodiments, the inner portions 125, 725, 135, 735 and or the rigid parts 120, 130, 720, 730 are formed from a rigid polymer material such as acrylonitrile butadiene styrene (ABS).

Figure 7A:
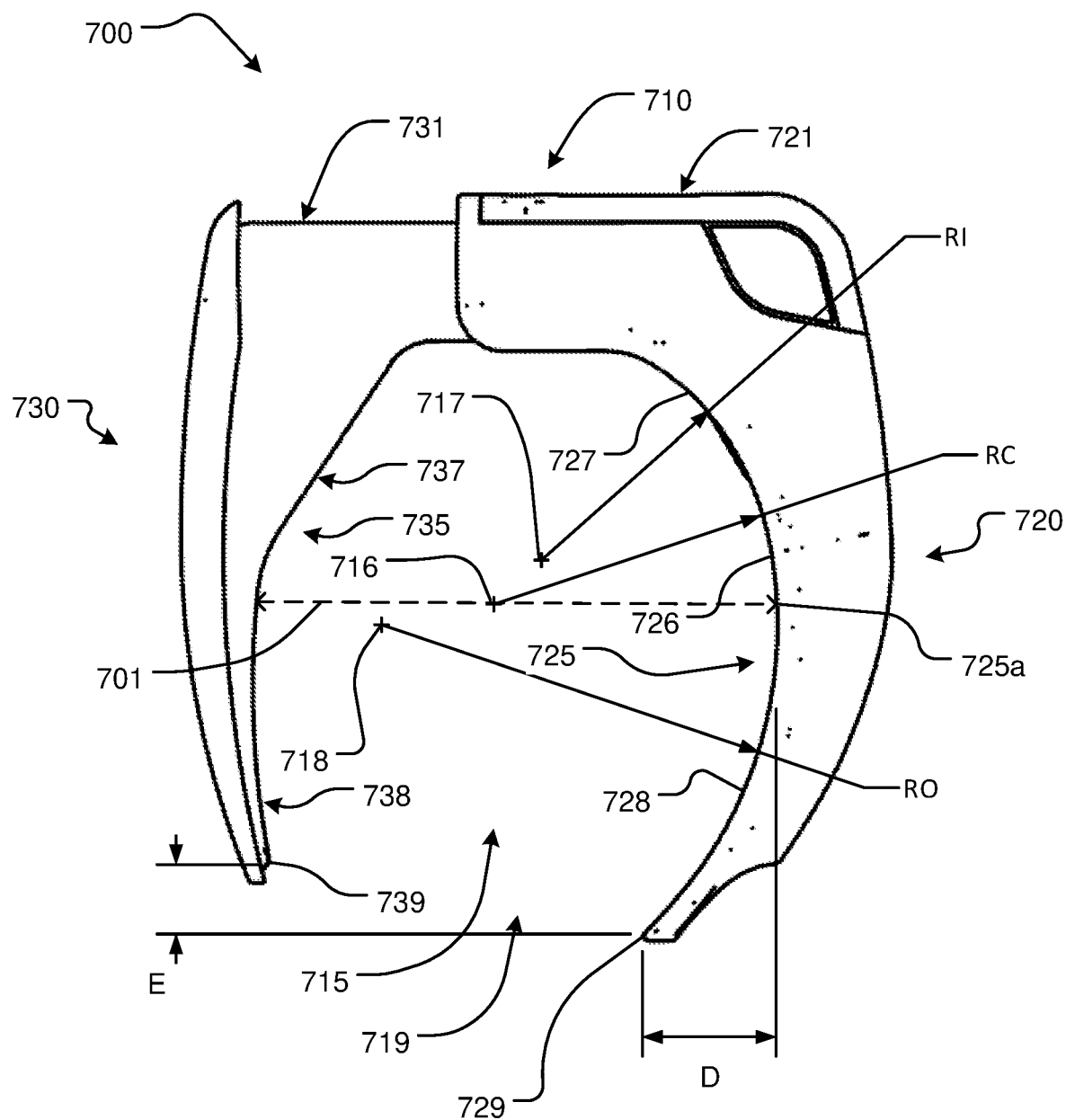
FIG. 7A is a transverse side view of a clamping device.
Figure 7B:
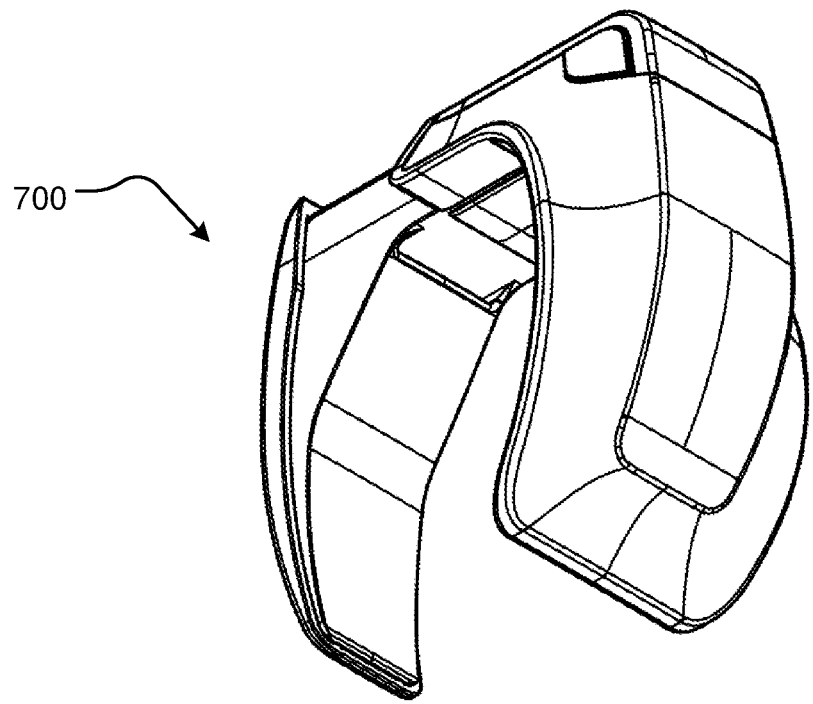
FIG. 7B is a perspective view of the clamping device of FIG. 7A from a posterior medial position.
Figure 7C:
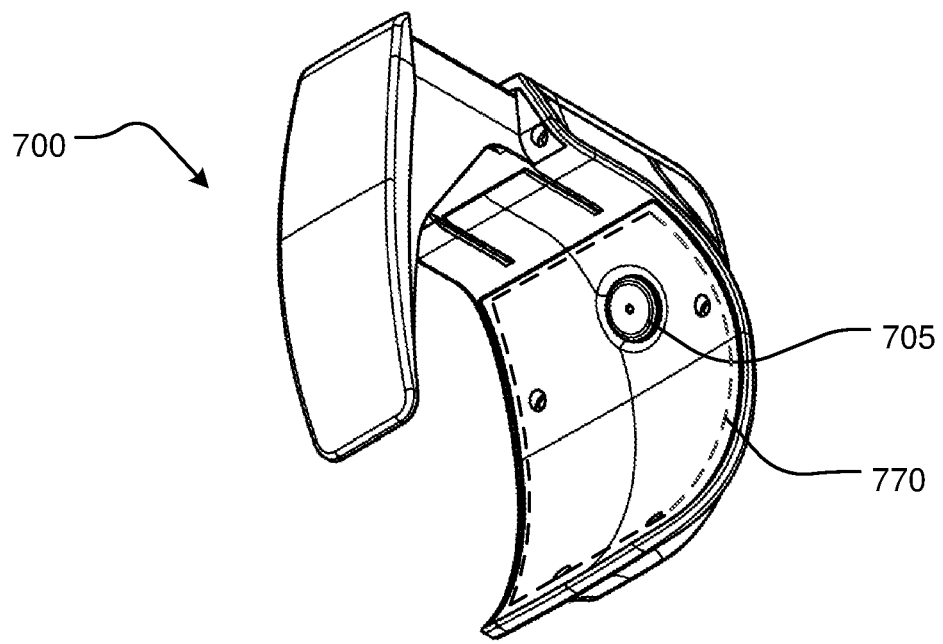
FIG. 7C is a perspective view of the clamping device of FIG. 7A from a posterior lateral position.
Figure 7D:
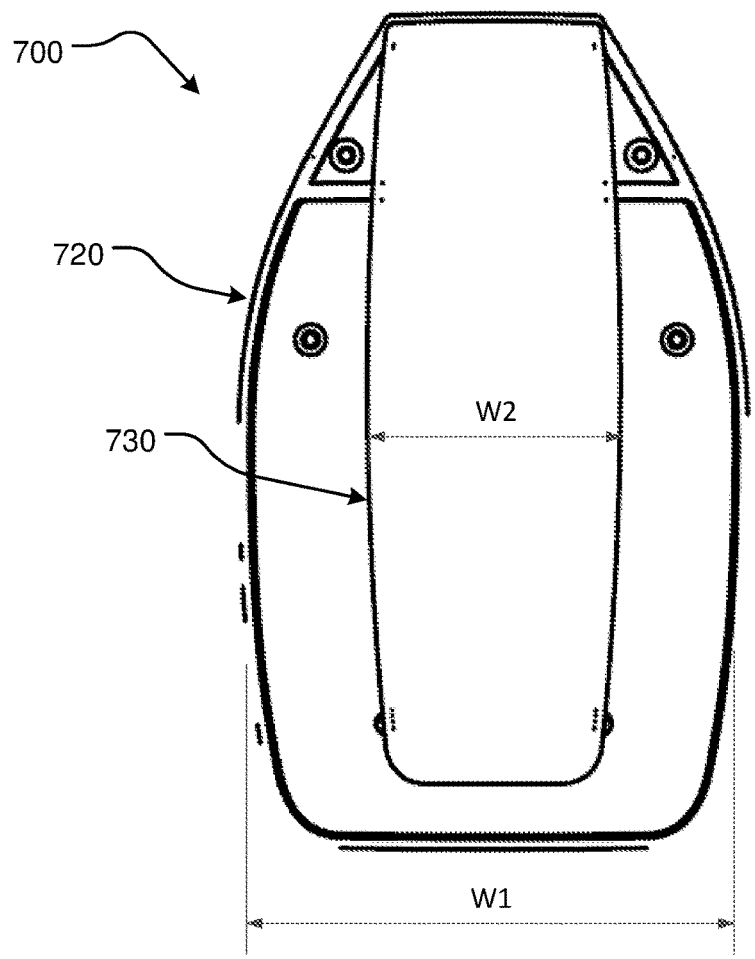
FIG. 7D is a lateral side view of the clamping device of FIG. 7A.
Figure 7E:
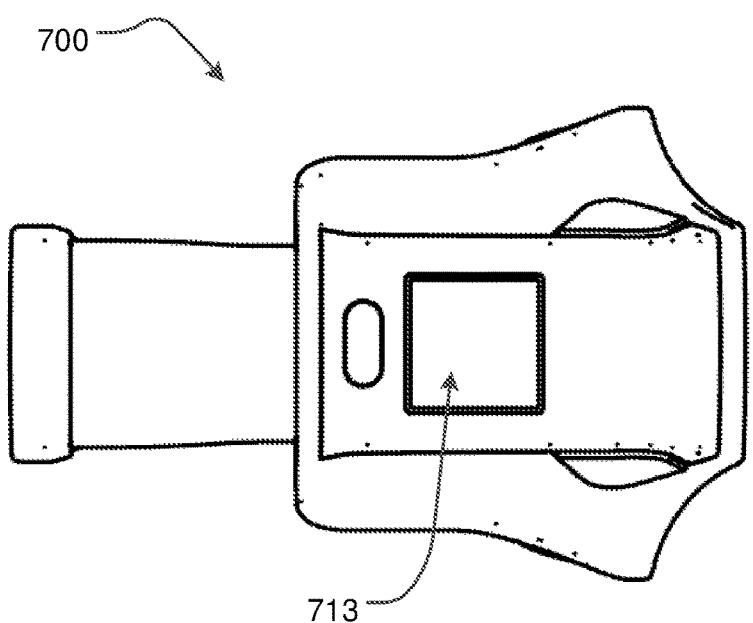
FIG. 7E is an anterior view of the clamping device of FIG. 7A.

The clamping device 700 may be generally asymmetric in shape when viewed from the side as shown in FIG. 7A. For example, the first part 720 is larger and wider than the second part 730. However, clamping device 700 is generally symmetric when seen in end view, as shown in FIG. 7D. The second inner profile 125, 725 has a shape with less curvature than the first inner profile 135, 735. The second inner profile 125, 725 may comprise a distal section 738 with a radius of curvature in the range of about 180 mm to about 220 mm. In some embodiments, the second inner profile 125, 725 may have a radius of curvature of about 200 mm. The curved distal section 738 may extend from a generally straight section 137, 737 to the distal tip 739. The radius of curvature of distal section 738 is, in the embodiments device 700 shown, greater than the radius of curvature of each of the curved portions 726, 727 and 728 of the first inner profile 725.

Figure 8:
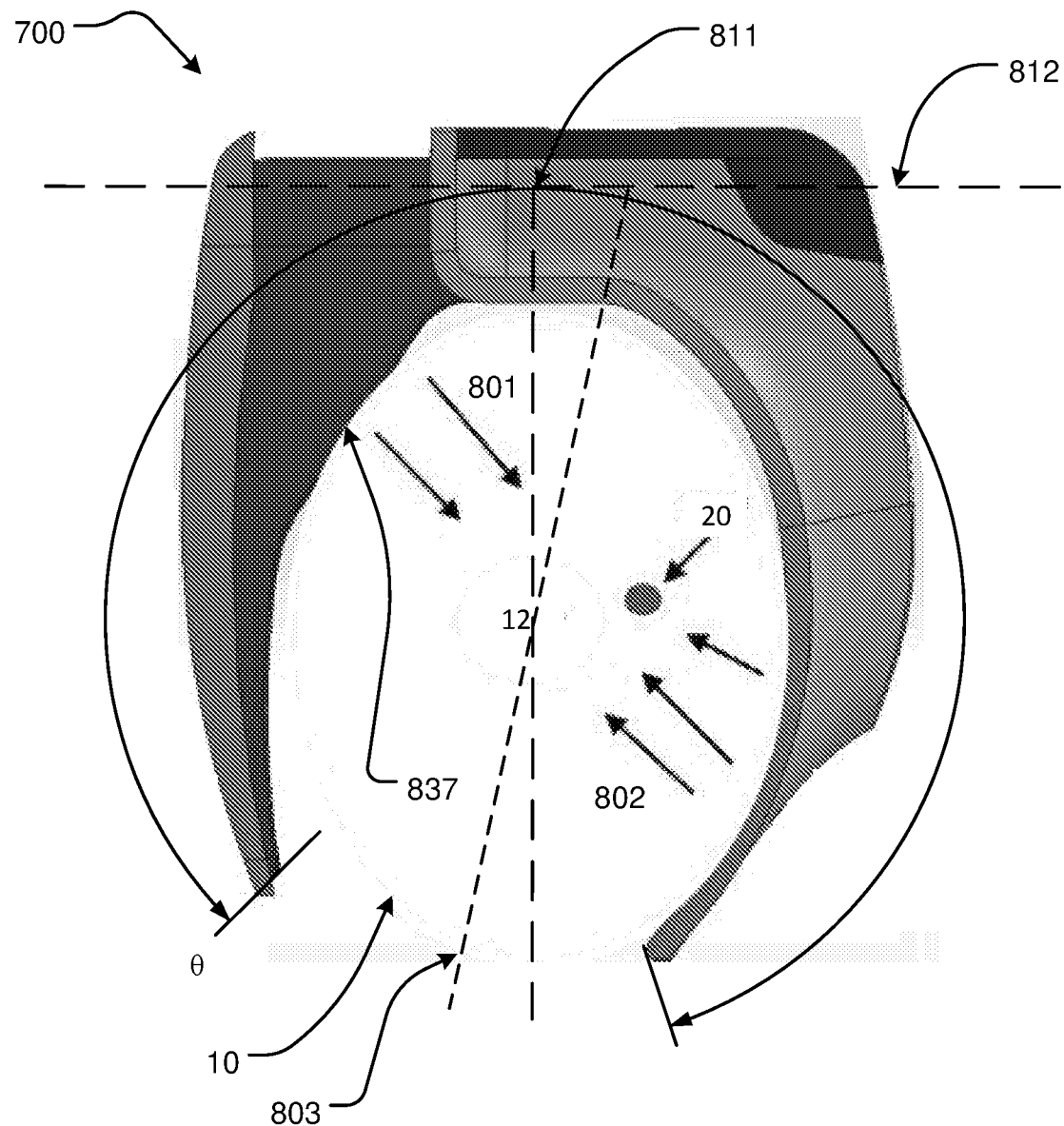
FIG. 8 is a schematic diagram of the clamping device of FIG. 7A placed on a human upper arm shown in transverse cross-section.

Referring to FIG. 8, the clamping device 100, 700, 2600 may therefore partially encircle the human limb 10 over a range of encirclement angles θ between about 280° and about 315°. The angle θ is measured about an axis at the centre of the recess 115, 715 when the clamping device 100, 700, 2600 is in the clamped configuration. Said axis may, for example, be located within a bone such as the humerus 12 within the human limb 10. In some embodiments, the range of encirclement angles is between about 295° and about 305°. For example, the range of encirclement may be about 300°.

As is evident from FIG. 8, the encirclement of the clamping device 700 about a limb 10 in the clamped configuration leaves opening 719 between the distal ends of the opposed first and second rigid parts 720, 730. For device 700, because it is generally asymmetrical (in side view), the opening 719 is not centred with respect to a mid-point 811 of the length of the coupling portion 710. In other words, the centre 803 of the opening 719 is acutely or obtusely angled (i.e. not perpendicular) relative to a line 812 along the direction of expansion and contraction of the first and second rigid parts 720, 730.

When the clamping device 100, 700, 2600 is clamped onto the human limb 10 in the clamped configuration, pressure is applied to the human limb 10 along directions 801, 802 as a result of the combination of the curvature of the first inner profile 125, 725 and the straight section 137, 837 of the second inner profile 135, 735.

Figure 9:
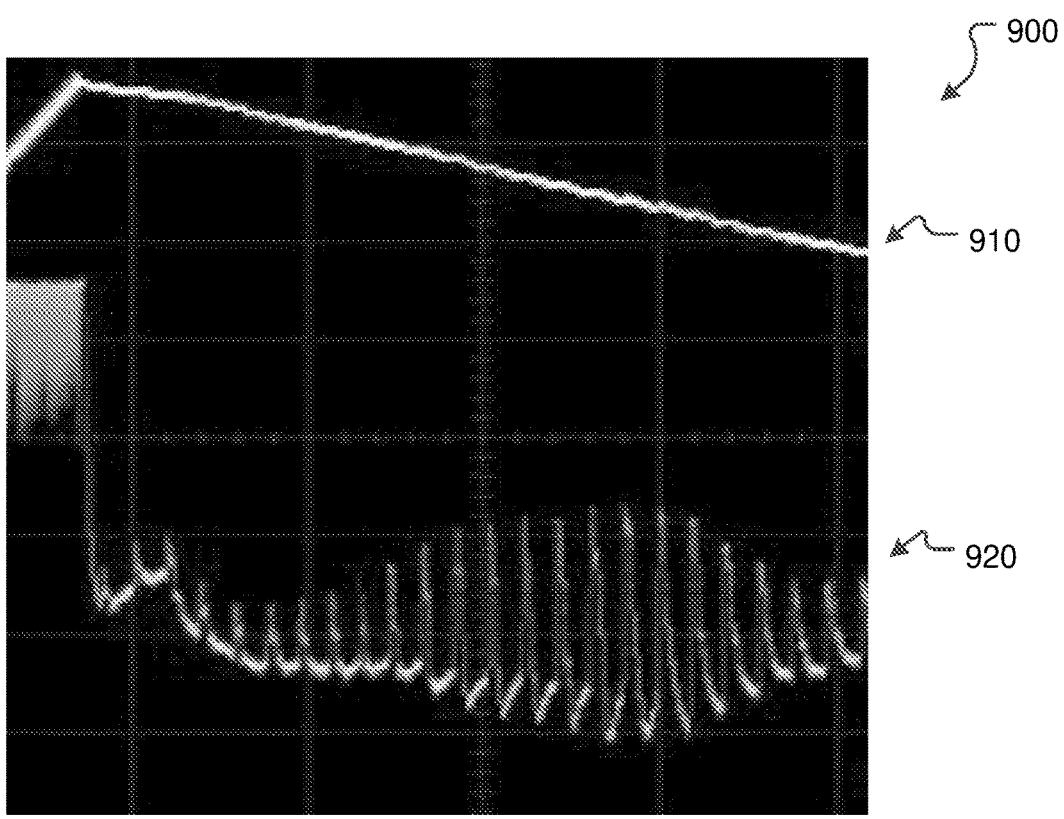
FIG. 9 is a plot of sensed pressure and calculated pressure.

Referring to FIG. 9, an exemplary pressure plot 900 as a function of time during a blood pressure measurement shows the pressure 910 in the expandable element 170, 770, 2670 sensed by the pressure sensing componentry 105, 705. A reliable and strong differential pressure signal 920 (or oscillatory component of the pressure) can be calculated from the pressure 910 when the clamping device 100, 700, 2600 is reliably and consistently clamped onto the human limb 10. The differential (oscillatory) pressure signal 920 may, for example, be indicative of the blood pressure in the brachial artery 20. Accurate blood pressure values that are calculated may be displayed on a display 113, 713.

Figure 10:
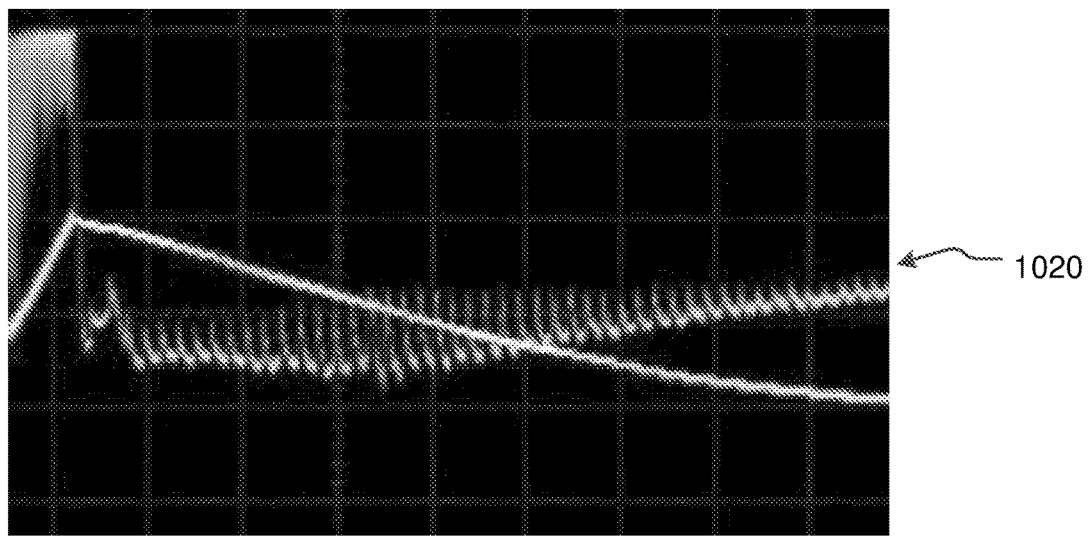
FIG. 10 is a plot of sensed pressure and calculated pressure.

Referring to FIG. 10, if the clamping device 100, 700, 2600 is dislodged or moves off the human limb 10 during pressure measurement, then the calculated differential pressure signal 1020 may be smaller than the differential pressure signal 920 obtained from a stably clamped clamping device 100, 700, 2600. Movement of the clamping device 100, 700, 2600 during measurement may lead to inaccurate blood pressure measurements.

Variations and/or modifications may be made to the above-described embodiments, without departing from the broad general scope of the present disclosure. The present embodiments are, therefore, to be considered in all respects as illustrative and not restrictive.

The invention claimed is:

1. A clamping device for reducing blood flow in a human limb comprising:
   a first rigid part having a first inner profile;
   a second rigid part having a second inner profile generally facing the first inner profile; and
   a coupling portion that telescopically couples the first rigid part and second rigid part to each other,
   wherein the first inner profile has a degree of concavity that is greater than a degree of concavity of the second inner profile,
   wherein the first and second inner profiles define a recess, and the recess is shaped to enable the clamping device to be positioned on the human limb,
   wherein the first inner profile has a central portion with a central curvature that is less than an outer curvature at an outer portion of the curved first inner profile,
   wherein the central curvature is greater than an inner curvature at an inner portion of the curved surface,
   wherein a distal tip of the first inner profile extends further away than the second inner profile by an extension in the range of about 8 mm to 20 mm,
   wherein the central curvature is defined by a central radius in the range of about 56 mm to about 76 mm, wherein the outer curvature is defined by an outer radius in the range of about 77 mm to about 105 mm, and wherein the inner curvature is defined by an inner radius in the range of about 40 mm to about 55 mm,
   wherein the clamping device is configured to shift between an expanded configuration and a clamped configuration, and
   wherein the first and second inner profiles are arranged to apply pressure against the human limb when the device is in the clamped configuration and thereby apply pressure to blood vessels in the human limb and reduce blood flow through the blood vessels.

2. The clamping device of claim 1, wherein a first distal end portion of the first rigid part is angled inwardly toward the coupling portion by a greater degree than a second distal end portion of the second rigid part.

3. The clamping device of claim 1, wherein the first inner profile includes a plurality of profile portions, wherein the first inner profile is curved and each of the profile portions is concave and has a different curvature.

4. The clamping device of claim 3, wherein the different curvatures of the profile portions are defined by a plurality of axes located within the recess, and the axes are offset from each other.

5. The clamping device of claim 1, wherein the coupling portion comprises a first base portion attached to the first rigid part and a second base portion attached to the second rigid part, and the first base portion is configured to receive at least a part of the second base portion.

6. The clamping device according to claim 1, wherein the second rigid part defines a straight portion angled with respect to the second rigid part.

7. The clamping device according to claim 1, wherein the second inner profile is partly straight and partly curved.

8. The clamping device according to claim 1, further comprising pressure sensing componentry comprising any one or more of: a pressure sensing component, an ultrasonic transmitter, an ultrasonic sensing component, and a piezoelectric pressure transducer.

9. The clamping device according to claim 8, wherein the pressure sensing component and/or ultrasonic transmitter is configured to transmit ultrasonic waves towards an artery in the human limb when in the clamping device is positioned on the limb, and the pressure sensing component senses reflected ultrasonic waves.

10. The clamping device according to claim 9, wherein at least part of the pressure sensing componentry and/or ultrasonic transmitter is located to transmit ultrasonic waves oriented at an angle relative to the length of the artery in the range of 85° to 95°.

11. The clamping device according to claim 8, further comprising:
an expandable element arranged at least partly along the inner profile, wherein the expandable element is inflatable to apply pressure to the limb, and deflatable to reduce the pressure, when the clamping device is positioned on the limb; and
inflation components for controlling the inflation of the expandable element in a predetermined manner for blood pressure measurements.

12. The clamping device according to claim 11, wherein the pressure sensing componentry is located adjacent the expandable element.

13. The clamping device according to claim 11, wherein the inflation components comprise:
a pump in fluid connection with the expandable element for inflating and deflating the expandable element; and
a controller connected to the pump for controlling the pump to inflate and deflate the expandable element in a predetermined manner for obtaining blood pressure measurements over a period of time.

14. The clamping device according to claim 8, wherein the at least one processor is configured to:
determine a baseline pressure using the at least one pressure sensing componentry.

15. The clamping device according to claim 14, wherein the at least one processor is configured to:
determine a change from the baseline pressure based on an output from the pressure sensing componentry.

16. The clamping device according to claim 15, wherein the at least one processor is configured to:
calculate a modified blood pressure measurement based on the baseline pressure and the output from the pressure sensing componentry.

17. The clamping device according to claim 15, wherein the processor is configured to determine a phase, echo time and/or frequency of pressure oscillation from the output of the pressure sensing componentry.

18. The clamping device according to claim 15, wherein the processor is configured to determine a change in phase, echo time and/or frequency of pressure oscillation from the output of the pressure sensing componentry.

19. The clamping device according to claim 15, wherein blood pressure measurements are repeated at a rate greater than any one or more of: once every 5 minutes, once every 2 minutes, once every minute, once every 30 seconds, once every 15 seconds, once every 10 seconds, once every 5 seconds, and once every second.

20. The clamping device according to claim 15, wherein the processor is configured to trigger an alarm signal if the determined change is greater than a predetermined threshold.

21. The clamping device according to claim 14, wherein the pressure sensing componentry is configured to sense pressure oscillations at a rate in the range of about 5 Hz to about 100 Hz.

22. The clamping device according to claim 9, further comprising at least one processor and wherein one of the processors is a controller configured to, any one or more of:
operate a pump to inflate the expandable element to a first pressure set-point;
operate the pump to inflate the expandable element to a second pressure set-point that is higher than the first set-point;
operate a pressure relief valve to deflate an expandable element that is inflatable to apply pressure to a limb, and deflatable to reduce the pressure; and
stop operation of the pressure relief valve.

23. The clamping device of claim 22, wherein the controller is configured to operate the pump to inflate the expandable element to a third pressure set point lower than the first set-point and the second-set point.

24. The clamping device according to claim 22, wherein the controller is configured to operate the pump to inflate the expandable element to a third pressure set point in the range of 20 mmHg to 60 mmHg.

25. The clamping device of claim 23, wherein the controller is configured to operate the transmitting component to transmit an ultrasonic wave when the expandable element is inflated to the third pressure set point.

26. The clamping device according to claim 1, further comprising a cushioning element disposed on at least one of the first inner profile and the second inner profile.

27. The clamping device of claim 26, wherein the cushioning element extends over the first inner profile and the second inner profile, is affixed to the first inner profile and is not affixed to the second inner profile.

28. The clamping device according to claim 1, wherein the first part and the second rigid part partially encircles a cross-section of the human limb when placed on the limb in the clamped configuration.

29. The clamping device according to claim 1, further comprising at least one releasable retention mechanism to retain the clamping device in the clamped configuration;
wherein the at least one retention mechanism is configured to allow the rigid body to adopt one of a plurality of retention positions in which the coupling portion is restrained from adopting the unclamped configuration.

* * * * *